United States Patent
Thibodeau

(10) Patent No.: US 9,827,186 B2
(45) Date of Patent: Nov. 28, 2017

(54) WAXES HAVING OIL-IN-WATER SELF-EMULSIFYING AND WATER GEL-FORMING PROPERTIES, COMPOSITIONS, USES AND METHODS RELATING TO SAME

(71) Applicant: INTERACTIVE SRL, Milan, P Iva (IT)

(72) Inventor: Alain Thibodeau, Quebec (CA)

(73) Assignee: INNOVACOS CORP., Mt. Arlington, NJ (US)

( * ) Notice: Subject to any disclaimer, the term of this patent is extended or adjusted under 35 U.S.C. 154(b) by 124 days.

(21) Appl. No.: 14/773,208

(22) PCT Filed: Mar. 6, 2014

(86) PCT No.: PCT/CA2014/050182
§ 371 (c)(1),
(2) Date: Sep. 4, 2015

(87) PCT Pub. No.: WO2014/134732
PCT Pub. Date: Sep. 12, 2014

(65) Prior Publication Data
US 2016/0022567 A1    Jan. 28, 2016

Related U.S. Application Data
(60) Provisional application No. 61/774,129, filed on Mar. 7, 2013.

(51) Int. Cl.
*A61K 31/21*    (2006.01)
*A61K 8/92*    (2006.01)
(Continued)

(52) U.S. Cl.
CPC ............... *A61K 8/92* (2013.01); *A61K 8/042* (2013.01); *A61K 8/062* (2013.01); *A61K 8/34* (2013.01);
(Continued)

(58) Field of Classification Search
CPC . A61K 8/92; A61K 8/34; A61K 8/922; A61K 8/37; A61K 8/042; A61K 8/375;
(Continued)

(56) References Cited

U.S. PATENT DOCUMENTS

| | | | |
|---|---|---|---|
| 4,454,113 A | 6/1984 | Hemker | |
| 4,719,103 A | 1/1988 | Krevald et al. | |
| 2012/0035130 A1 | 2/2012 | Peter et al. | |

FOREIGN PATENT DOCUMENTS

| | | |
|---|---|---|
| EP | 2213336 A2 | 8/2010 |
| WO | 2012120290 A2 | 9/2012 |

OTHER PUBLICATIONS

Happi, www.happi.com/2010-09/view features/formulating-natural-products/, p. 1-5.*
(Continued)

*Primary Examiner* — T. Victor Oh
(74) *Attorney, Agent, or Firm* — Banner & Witcoff, Ltd.

(57) ABSTRACT

The present invention relates to waxes useful for cosmetic applications having stable oil-in-water emulsion-forming properties and, in some embodiments, stable gel-in-water-forming properties. In some embodiments, the waxes exhibit self-emulsifying properties, and can be produced without the addition of any other substances to achieve the emulsion (e.g., co-emulsifiers, hydrophilic polymers, polar surfactants, rheological modifiers, gelling agents). The waxes generally comprise: (a) polyglyceryl fatty acid ester, (b) a glycerol fatty acid ester, and 9c) a fatty alcohol. In particular embodiments, the polyglyceryl fatty acid ester can be a
(Continued)

polyglyceryl-2, -3, or -4 fatty acid ester, and the fatty chain lengths of (a)-(c) can range from C12 to C22. In more particular embodiments, the waxes can comprise polyglyceryl stearate, glyceryl stearate, and stearyl alcohol. Gels, oil-in-water emulsions, and other compositions produced from the waxes, as well as uses and methods relating thereto, are also disclosed.

16 Claims, 1 Drawing Sheet

(51) Int. Cl.
    *A61Q 19/00*      (2006.01)
    *C11B 11/00*      (2006.01)
    *C08L 91/06*      (2006.01)
    *A61K 8/34*      (2006.01)
    *A61K 8/37*      (2006.01)
    *A61K 8/39*      (2006.01)
    *A61K 8/04*      (2006.01)
    *A61K 8/06*      (2006.01)

(52) U.S. Cl.
    CPC ............. *A61K 8/342* (2013.01); *A61K 8/37* (2013.01); *A61K 8/375* (2013.01); *A61K 8/39* (2013.01); *A61K 8/922* (2013.01); *A61Q 19/00* (2013.01); *A61Q 19/007* (2013.01); *C08L 91/06* (2013.01); *C11B 11/00* (2013.01)

(58) Field of Classification Search
    CPC .......... A61K 8/39; A61K 8/342; A61K 8/062; A61K 31/21; A61Q 19/007; A61Q 19/00; C08L 91/06; C11B 11/00
    USPC ........................................................ 514/506
    See application file for complete search history.

(56) References Cited

OTHER PUBLICATIONS

Supplementary European Search Report for EP 14 76 0625, dated Mar. 18, 2016; 7 pages.
Innovacos, PolyAquol 2W, Technical Data Sheet, Apr. 2013 (Apr. 2013).
Liebert, M.A. "Final Report on the Safety Assessment of Stearyl Alcohol, Oleyl Alcohol, and Octyl Dodecanol" 1985, Journal of the American College of Toxicology 4(5): 1-29.
PCT/CA2014/050182, International Search Report and Written Opinion, dated Jun. 17, 2014.
EPO Communication pursuant to Article 94(3) EPC for EP 14760625.5, 4 pages, dated Mar. 31, 2017.

* cited by examiner

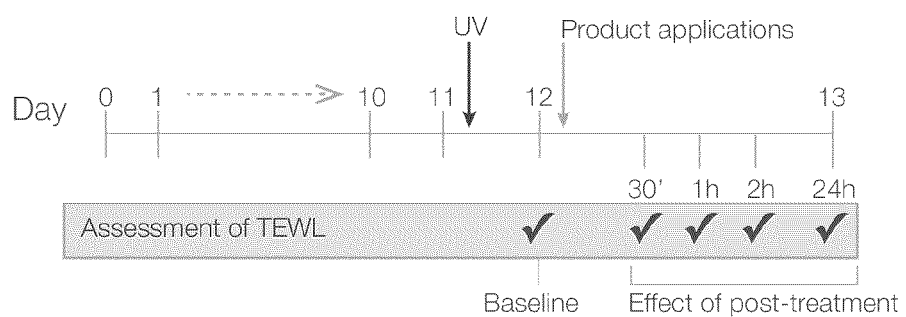

WAXES HAVING OIL-IN-WATER SELF-EMULSIFYING AND WATER GEL-FORMING PROPERTIES, COMPOSITIONS, USES AND METHODS RELATING TO SAME

CROSS REFERENCE TO RELATED APPLICATIONS

This application is a National Entry Application of PCT application Ser. No. PCT/CA2014/050182 filed on Mar. 6, 2014 and published in English under PCT Article 21(2), which itself claims benefit of U.S. provisional application Ser. No. 61/774,129, filed on Mar. 7, 2013. All documents above are incorporated herein in their entirety by reference.

FIELD OF THE INVENTION

The present invention relates to waxes having oil-in-water self-emulsifying properties and water gel-forming properties. More specifically, the waxes comprise a polyglyceryl fatty acid ester, a glycerol fatty acid ester, and a fatty alcohol.

BACKGROUND OF THE INVENTION

An emulsion consists of two immiscible liquids mixed together with small droplets of one liquid dispersed in the other liquid. The dispersion is usually not stable and all the droplets "clump" together over time to form two layers. An emulsion can be stabilized by inhibiting coalescence (i.e., preventing the droplets from clumping together) by the presence of surfactant molecules. The majority of emulsions can be classified according to the chemical nature of the liquids, such as oil-in-water (O/W) or water-in-oil (W/O).

O/W emulsions are widely used in the cosmetic and other industries due to their sensorial profile characterized by light skin feel, non-greasy texture, and high spreadability index, as well as for their easy production methods. Gel-in-water systems (water gels) having similar sensorial characteristics can be achieved using a thickening agent (e.g., acrylate polymers) mixed with water. Acrylate polymers are also able to produce O/W emulsions, and, in general, stable O/W emulsions require ionic surfactants or a non-ionic ethoxylated/propoxylated product. However, the presence of ionic surfactants can lead to skin sensitization and skin irritation, and the presence of acrylate polymers, ethoxylated and propoxylated products are not desirable to produce "green" (environmentally-friendly) emulsions. Thus, there exists a need for O/W emulsions and water gels lacking ionic surfactants, acrylate polymers, ethoxylated or propoxylated emulsifiers.

The present description refers to a number of documents, the content of which is herein incorporated by reference in their entirety.

SUMMARY OF THE INVENTION

The present invention relates to the surprising discovery of a wax having O/W self-emulsifying properties, due to synergic action between its principal components. The present invention also relates to a wax that is able to produce stable O/W emulsions and a stable water gel system without the addition of any other substance(s) to achieve the emulsion (e.g., other emulsifier, or co-emulsifiers, hydrophilic polymers, polar surfactants, rheological modifiers, gelling agents).

In one aspect, the present invention relates to a wax having oil-in-water (O/W) emulsion-forming properties, the wax comprising: (a) a polyglyceryl fatty acid ester, having a fatty acid carbon chain length of $n_1$; (b) a glycerol fatty acid ester, having a fatty acid carbon chain length of $n_2$; and (c) a fatty alcohol, having a fatty carbon chain length of $n_3$; wherein $n_1$, $n_2$, and $n_3$ are integers.

In another aspect, the present invention relates to a method for manufacturing the above mentioned wax, the method comprising combining: (a) a polyglyceryl fatty acid ester, having a fatty acid carbon chain length of $n_1$; (b) a glycerol fatty acid ester, having a fatty acid carbon chain length of $n_2$; and (c) a fatty alcohol, having a fatty carbon chain length of $n_3$; in amounts enabling the wax to form an oil-in-water (O/W) emulsion, wherein $n_1$, $n_2$, and $n_3$ are integers.

In some embodiments, the polyglyceryl fatty acid ester of (a) is a polyglyceryl-2 fatty acid ester, a polyglyceryl-3 fatty acid ester, or a polyglyceryl-4 fatty acid ester. In some embodiments: (i) the fatty acid of (a) is saturated; (ii) the fatty acid of (b) is saturated; (iii) the fatty alcohol of (c) is saturated; or (iv) any combination of (i) to (iii).

In some embodiments, each of $n_1$, $n_2$, and $n_3$ represent any integer in the range of 12 to 22, 14 to 20, or 16 to 18. In some embodiments, the difference between the integers represented by $n_1$ and $n_2$, $n_1$ and $n_3$, and $n_2$ and $n_3$ is less than or equal to 4, less than or equal to 3, less than or equal to 2, or less than or equal to 1. In some embodiments, $n_1=n_2=n_3$. In some embodiments, $n_1$, $n_2$, or $n_3$,=18.

In some embodiments, the above mentioned wax comprises: (i) about 20 to 50 parts of the polyglyceryl fatty acid ester; (ii) about 25 to 40 parts of the glycerol fatty acid ester; and (iii) about 25 to 35 parts of the fatty alcohol. In some embodiments, the above mentioned wax comprises about 35 to 45 parts of the polyglyceryl fatty acid ester.

In some embodiments, the polyglyceryl fatty acid ester of (a) is polyglyceryl stearate. In some embodiments, the polyglyceryl stearate is: polyglyceryl-2 stearate; polyglyceryl-3 stearate; polyglyceryl-4 stearate; or any combination thereof. In some embodiments, the polyglyceryl stearate is integrated according to the following stoichiometry: about 1.0 to about 2.0 equivalents of stearic acid esterified with 1.0 equivalent of polyglyceryl-2, polyglyceryl-3, polyglyceryl-4, or any combination thereof. In some embodiments, the polyglyceryl stearate is integrated according to the following stoichiometry: about 1.1 to about 1.2 equivalents of stearic acid esterified with 1.0 equivalent of polyglyceryl-2, polyglyceryl-3, polyglyceryl-4, or any combination thereof.

In some embodiments, the glycerol fatty acid ester of (b) is glyceryl stearate. In some embodiments, the glyceryl stearate is integrated according to the following stoichiometry: about 0.8 to 1.2 equivalents of sufficiently pure stearic acid, esterified with 1.0 equivalent of sufficiently pure glycerol. In some embodiments, the glyceryl stearate is integrated according to the following stoichiometry: about 1.0 equivalent of sufficiently pure stearic acid, esterified with 1.0 equivalent of sufficiently pure glycerol.

In some embodiments, the fatty alcohol of (c) is stearyl alcohol.

In some embodiments, the above mentioned wax has self-emulsifying properties. In some embodiments, the above mentioned wax can form an O/W emulsion in the absence of a co-emulsifier, surfactant, rheological modifier, or gelling agent. In some embodiments, the above mentioned wax does not comprise a coemulsifier, surfactant, rheological modifier, gelling agent, or any combination thereof. In some embodiments, the above mentioned wax can form an O/W emulsion in the absence of an ionic surfactant, an ethoxylated product or a propoxylated product. In some embodiments, the above mentioned wax does not comprise an ionic surfactant, an ethoxylated product or a propoxylated product. In some embodiments, the above mentioned wax can form a stable O/W emulsion for at least 1 week at about 50° C. In some embodiments, the above mentioned wax can form a stable O/W emulsion for at least 2 weeks, 3 weeks or 1 month at about 50° C.

In some embodiments, the above mentioned wax has the ability of forming a gel in water. In some embodiments, the above mentioned wax can form a gel in water that is stable for at least 1 week at about 50° C. In some embodiments, the above mentioned wax can form a gel in water that is stable for at least 2 weeks, 3 weeks or one month at about 50° C.

In another aspect, the present invention relates to a gel comprising or produced from the wax defined above, and water. In some embodiments, the gel is stable for at least 1 week at about 50° C. In some embodiments, the gel is stable for at least 2 weeks, 3 weeks or one month at about 50° C. In some embodiments, the gel further comprises one or more preservatives. In some embodiments, the preservatives comprise at least one of phenoxyethanol and parabens.

In another aspect, the present invention relates to an oil-in-water emulsion comprising or produced from the wax defined above, an oil and water. In some embodiments, the oil-in-water emulsion comprises multilamellar vesicles. In some embodiments, the oil-in-water emulsion is stable for at least 1 week at about 50° C. In some embodiments, the oil-in-water emulsion is stable for at least 2 weeks, 3 weeks or 1 month at about 50° C. In some embodiments, the oil-in-water emulsion further comprises one or more preservatives. In some embodiments, the preservatives comprise at least one of phenoxyethanol and parabens. In some embodiments, the oil is sweet almond oil. In some embodiments, the oil-in-water emulsion does not comprise a co-emulsifier, a polar or ionic surfactant, an ethoxylated product, a propoxylated product, a rheological modifier, a gelling agent, or any combination thereof.

In some embodiments, the above mentioned wax, gel or oil-in-water emulsion is for use in a cosmetic or a cosmetic application.

In another aspect, the present invention relates to a composition comprising: (i) the wax as defined above; (ii) the gel as defined above; or (iii) the oil-in-water emulsion as defined above, and a suitable carrier.

In some embodiments, the above mentioned composition is a cosmetic composition.

In some embodiments, the above mentioned composition does not comprise a co-emulsifier, an ionic surfactant, an ethoxylated product, a propoxylated product, a rheological modifier, a gelling agent, or any combination thereof. In some embodiments, the above mentioned composition does not comprise a co-emulsifier, surfactant (e.g., polar or ionic), rheological modifier, gelling agent, or any combination thereof.

In some embodiments, the present invention provides a wax that can form an O/W emulsion in the absence of, or a gel-in-water or composition comprising the wax of the invention devoid of: (i) other emulsifier; (ii) co-emulsifier, (iii) surfactant (e.g., polar and/or ionic), (iv) rheological modifier, (v) gelling agent; (vi) an ethoxylated product; (vii) propoxylated product; or (viii) any combination of at least two of (i) to (vii)

In another aspect, the present invention relates to a method for reducing and/or preventing skin barrier function disruption, or for accelerating skin barrier function recovery or repair, the method comprising administering to the skin: (i) the wax as defined above; (ii) the gel as defined above; (iii) the oil-in-water emulsion as defined above; or (iv) the composition as defined above.

In another aspect, the present invention relates to a method for reducing trans-epidermal water loss (TEWL) and/or hydrating or moisturizing skin, the method comprising administering to the skin: (i) the wax as defined above; (ii) the gel as defined above; (iii) the oil-in-water emulsion as defined above; or (iv) the composition as defined above.

In another aspect, the present invention relates to the wax as defined above, the gel as defined above, the oil-in-water emulsion as defined above, or the composition as defined above, for use in: (a) reducing and/or preventing skin barrier function disruption; (b) accelerating skin barrier function recovery or repair; (c) reducing trans-epidermal water loss (TEWL); or (d) hydrating or moisturizing skin. In another aspect, the present invention relates to the use of the wax as defined above, the gel as defined above, the oil-in-water emulsion as defined above, or the composition as defined above, for: (a) reducing and/or preventing skin barrier function disruption; (b) accelerating skin barrier function recovery or repair; (c) reducing trans-epidermal water loss (TEWL); or (d) hydrating or moisturizing skin. In another aspect, the present invention relates to the use of the wax as defined above, the gel as defined above, the oil-in-water emulsion as defined above, or the composition as defined above, for the manufacture of a product for: (a) reducing and/or preventing skin barrier function disruption; (b) accelerating skin barrier function recovery or repair; (c) reducing trans-epidermal water loss (TEWL); or (d) hydrating or moisturizing skin.

Other objects, advantages and features of the present invention will become more apparent upon reading of the following non-restrictive description of specific embodiments thereof, given by way of example only with reference to the accompanying drawings.

BRIEF DESCRIPTION OF THE DRAWING

In the appended drawing:

FIG. 1 shows schematically a treatment schedule for healthy volunteers tested with a water gel formulation of the present invention.

DESCRIPTION OF ILLUSTRATIVE EMBODIMENTS

Headings, and other identifiers, e.g., (a), (b), (i), (ii), etc., are presented merely for ease of reading the specification and claims. The use of headings or other identifiers in the specification or claims does not necessarily require the steps or elements be performed in alphabetical or numerical order or the order in which they are presented.

In the present description, a number of terms are extensively utilized. In order to provide a clear and consistent understanding of the specification and claims, including the scope to be given such terms, the following definitions are provided.

General Definitions

The use of the word "a" or "an" when used in conjunction with the term "comprising" in the claims and/or the specification may mean "one" but it is also consistent with the meaning of "one or more", "at least one", and "one or more than one".

Throughout this application, the term "about" is used to indicate that a value includes the standard deviation of error for the device or method being employed to determine the value. In general, the terminology "about" is meant to designate a possible variation of up to 10%. Therefore, a variation of 1, 2, 3, 4, 5, 6, 7, 8, 9 and 10% of a value is included in the term "about".

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps.

As used herein, the term "consists of" or "consisting of" means including only the elements, steps, or ingredients specifically recited in the particular claimed embodiment or claim.

By "pharmaceutically acceptable," "physiologically tolerable," "dermatologically acceptable", or "pharmaceutically suitable", "physiologically suitable," "dermatologically suitable" and grammatical variations thereof, as they refer to compositions, carriers, diluents, and reagents or other ingredients of the formulation, can be used interchangeably and represent that the materials are capable of being administered without the production of undesirable physiological effects such as rash, burning, irritation or other deleterious effects to such a degree as to be intolerable to the recipient thereof.

As used herein, the term "cosmetically acceptable", "cosmetically suitable" and grammatical variations thereof, as they refer to compositions, carriers, diluents, and reagents or other ingredients of the formulation, represent that the materials used and final composition are not irritating or otherwise harmful to the patient in general and to the skin, in particular, and preferably are pleasant and well tolerated with respect to general appearance, pH, color, smell and texture (feel), that they are not, for example, unacceptably sticky (tacky), oily or drying, and that they do spread easily, absorb into the skin at an acceptable rate of absorption, and are generally moisturizing.

As used herein, the term "subject" is intended to include human and non-human animals. Exemplary human subjects include a human patient having a disorder, e.g., a disorder described herein, or a normal subject. The term "non-human animals" includes all vertebrates, e.g., non-mammals (such as chickens, amphibians, reptiles) and mammals, such as non-human primates, domesticated and/or agriculturally useful animals, e.g., sheep, dog, cat, cow, pig, horse, etc.

As used herein, the term "treat" or "treating" a subject having a disorder refers to subjecting the subject to a regimen, e.g., the administration of a composition of the present invention such that at least one symptom of the disorder is cured, healed, alleviated, relieved, altered, remedied, ameliorated, or improved. Treating includes administering an amount effective to alleviate, relieve, alter, remedy, ameliorate, improve or affect the disorder or the symptoms of the disorder. The treatment may inhibit deterioration or worsening of a symptom of a disorder.

Waxes

In one aspect, the present invention relates to a wax having oil-in-water (O/W) emulsion-forming properties. The wax comprises three principal components: (a) a polyglyceryl fatty acid ester; (b) a glycerol fatty acid ester; and (c) a fatty alcohol; wherein $n_1$, $n_2$, and $n_3$ are integers representing the fatty chain lengths of (a), (b) and (c), respectively. Each of these three principal components interacts with each other to confer advantages properties (e.g., self-emulsification, water gel-forming ability, and/or stability) to the waxes of the present invention and compositions produced therefrom.

As used herein, the expression "polyglyceryl fatty acid ester" includes polyglycerol esters of fatty acids, as well as derivatives, variants and/or analogs of these compounds (e.g., relatively minor chemical/structural modifications of polyglyceryl fatty acid esters) that do not significantly affect the ability of a wax of the present invention to form a stable, self-emulsifying O/W emulsion and/or a stable water gel. In some embodiments, the polyglyceryl fatty acid esters can be isolated from natural sources, can be synthetic, or a mixture thereof. In some embodiments, polyglyceryl fatty acid ester(s) can be obtained by esterifying a polyglycerol and a fatty acid using methods well known in the art.

As used herein, the expression "glycerol fatty acid ester" includes glycerol (glycerol-1: one glycerol monomeric unit) esters of fatty acids and glycerin (glycerol-1: one glycerol monomeric unit) fatty acid esters, as well as derivatives, variants and/or analogs of these compounds (e.g., relatively minor chemical/structural modifications of glycerol fatty acid esters) that do not significantly affect the ability of a wax of the present invention to form a stable, self-emulsifying O/W emulsion and/or a stable water gel. In some embodiments, the glycerol fatty acid esters can be isolated from natural sources, can be synthetic, or a mixture thereof. In some embodiments, glycerol fatty acid ester(s) can be obtained by esterifying a glycerol and a fatty acid using methods well known in the art.

As used herein, the expression "fatty alcohol" includes aliphatic alcohols generally having at least eight carbon atoms and an alcohol group, as well as derivatives, variants and/or analogs of these compounds (e.g., relatively minor chemical/structural modifications of fatty alcohols) that do not significantly affect the ability of a wax of the present invention to form a stable, self-emulsifying O/W emulsion and/or a stable water gel. In some embodiments, the fatty alcohol(s) can be isolated from natural sources, can be synthetic, or a mixture thereof.

As used herein, "stable" refers to a system (e.g., an emulsion or gel) that exhibits no perceptible separation, syneresis, or change in texture for a fixed period of time at a given temperature. In some embodiments, an emulsion or gel of the present invention remains stable for at least 1 day, 2 days, 1 week, 2 weeks, 3 weeks or 1 month at about 50° C. In some embodiments, an emulsion or gel of the present invention remains stable for at least 1 month at about 50° C.

In some embodiments, the waxes of the present invention have self-emulsifying properties. As used herein, "self-emulsifying" or "auto-emulsifying" refers to the ability to form a stable system or emulsion (e.g., O/W emulsion) in the context of the present invention without the need of adding another substance (e.g., a further emulsifier or co-emulsifier, hydrophilic polymer, polar surfactant, rheological modifier, gelling agent or other stabilizing agent), other than the polyglyceryl fatty acid ester, glycerol fatty acid ester, and fatty alcohol comprised in the waxes of the present invention.

In some embodiments, waxes and other compositions of the present invention can form O/W emulsions in the absence of an ionic surfactant, an ethoxylated product, a propoxylated product, a rheological modifier, or a gelling agent. In some embodiments, waxes and other compositions of the present invention do not comprise an ionic surfactant, an ethoxylated product, a propoxylated product, a rheological modifier, or a gelling agent. As used herein, "ethoxylated or propoxylated products" can include ethoxylated or propoxylated fatty alcohols, fatty acids, fatty amines, or other compounds produced by ethoxylation or propoxylation.

In some embodiments, the polyglyceryl fatty acid ester, glycerol fatty acid ester, and fatty alcohol comprised in the waxes of the present invention can have fatty chains that are saturated or unsaturated, straight or branch chained, substituted or unsubstituted. They can also independently have various fatty chain lengths. In some embodiments, the fatty chain lengths can independently range from, at least 8, 12 to 22, from 14 to 20, or from 16 to 18. In some embodiments, the difference between any two of the fatty chain lengths of the polyglyceryl fatty acid ester, glycerol fatty acid ester, and fatty alcohol comprised in the waxes of the present invention can be less than or equal to 4, less than or equal to 3, less than or equal to 2, or less than or equal to 1. In some embodiments, the polyglyceryl fatty acid ester, glycerol fatty acid ester, and fatty alcohol comprised in the waxes of the present invention can have the same fatty chain lengths (i.e., $n_1=n_2=n_3$). In some embodiments, one or more of the fatty chain lengths can be 18. Preferred fatty chains are those from, for example, palmitic, palmic, oleic, lauric, myristic, stearic, hydroxystearic, behenic acid, or mixtures thereof. It would be understood by the skilled person that a preparation of a specific fatty acid and/or fatty alcohol having a given carbon chain length (e.g., when the preparation is obtained/purified from natural sources) may contain fatty acid and/or fatty alcohol species having other carbon chain lengths present to a lesser degree. Accordingly as used herein, reference to an individual fatty acid and/or fatty alcohol species (e.g., having a particular carbon chain length, or derived from a particular fatty acid such as palmitic, palmic, oleic, lauric, myristic, stearic, hydroxystearic, behenic acid, or mixtures thereof) is meant to refer to the main species of fatty acid or fatty alcohol that is found in the given preparation, but does not necessarily exclude the presence of other fatty acids or fatty alcohols in lesser relative amounts, as long as the other fatty acids or fatty alcohols do not interfere with the preparation of a wax, emulsifier, emulsion, or composition of the present invention.

In some embodiments, waxes of the present invention can comprise: (i) about 20 to about 50 parts of the polyglyceryl fatty acid ester; (ii) about 25 to about 40 parts of the glycerol fatty acid ester; and (iii) about 25 to about 35 parts of the fatty alcohol. In some embodiments, the wax comprises about 35 to about 45 parts (preferably between about 35 to about 40 parts) of the polyglyceryl fatty acid ester. In some embodiments, waxes of the present invention can comprise the polyglyceryl fatty acid ester in a range having a lower limit of about 20, 21, 22, 23, 24, 25, 26, 27, 28, 29, 30, 31, 32, 33, 34, or 35 parts and an upper limit of about 36, 37, 38, 39, 40, 41, 42, 43, 44, 45, 46, 47, 48, 49, or 50 parts. In some embodiments, waxes of the present invention can comprise the glycerol fatty acid ester in a range having a lower limit of about 25, 26, 27, 28, 29, 30, or 31 parts and an upper limit of about 32, 33, 34, 35, 36, 37, 38, 39, or 40 parts. In some embodiments, waxes of the present invention can comprise the fatty alcohol in a range having a lower limit of about 25, 26, 27, 28, or 29 and an upper limit of about 30, 31, 32, 33, 34, or 35 parts. As used herein, "parts" refers to weigh ratios (i.e., parts-by-weight).

In some embodiments, the polyglyceryl fatty acid ester can be a polyglyceryl-X fatty acid ester, wherein X is any suitable integer representing the number of glycerol monomeric units, such as a polyglyceryl-2 fatty acid ester, a polyglyceryl-3 fatty acid ester, or a polyglyceryl-4 fatty acid ester.

In some embodiments, the polyglyceryl fatty acid ester can be polyglyceryl stearate, the glycerol fatty acid ester can be glyceryl stearate, and the fatty alcohol can be stearyl alcohol.

In some embodiments, waxes of the present invention have the ability of forming a gel-in-water (water gel). In some embodiments, the above mentioned wax can form a gel in water that is stable for at least one week at about 50° C. In some embodiments, the above mentioned wax can form a gel in water that is stable for at least 2 weeks, 3 weeks or one month at about 50° C.

In some aspects, the present invention relates to emulsions (e.g., O/W emulsions), gels (water gels), and other compositions produced from or comprising the waxes of the present invention. In some embodiments, the emulsions, gels and other compositions are stable for at least 1 week at 50° C. In some embodiments, the emulsions, gels and other compositions are stable for at least 2 weeks, 3 weeks or one month at 50° C. In some embodiments, the emulsions, gels and other compositions can comprise one or more preservatives (e.g., phenoxyethanol and parabens).

In some embodiments, the above mentioned wax, gel or O/W emulsion is for use in a cosmetic or a cosmetic application.

In another aspect, the present invention relates to a method for manufacturing the above mentioned wax, the method comprising combining: (a) a polyglyceryl fatty acid ester, having a fatty acid carbon chain length of $n_1$; (b) a glycerol fatty acid ester, having a fatty acid carbon chain length of $n_2$; and (c) a fatty alcohol, having a fatty carbon chain length of $n_3$; in amounts enabling the wax to form an oil-in-water (O/W) emulsion, wherein $n_1$, $n_2$, and $n_3$ are integers.

Wax Preparation

Each of the principal components of the waxes of the present invention can be obtained by processes and methods well known in the art. For example, polyglyceryl stearate can be obtained esterifying about 1.0 to about 2.0 equivalents of stearic acid with 1.0 equivalent of polyglycerol (e.g., polyglyceryl-2 (diglycerol: two glycerol monomeric units), polyglyceryl-3 (triglycerol: three glycerol monomeric units), polyglyceryl-4 (tetraglycerol: four glycerol monomeric units)). In some embodiments, the polyglyceryl stearate can be obtained by esterifying about 1.1 to about 1.2 equivalents of stearic acid with 1.0 equivalent of polyglycerol (polyglyceryl-2, polyglyceryl-3, polyglyceryl-4). As used herein, "polyglycerol-n" where n is an integer, refers to a polymer of glycerol monomers in which n refers to the number of glycerol monomers present in the polyglycerol. It would be understood by the skilled person that the expression "polyglycerol-n" refers to the main species of polyglycerol that is present in a preparation, and that other polyglycerols may also be present to a lesser degree. Accordingly, the expression "polyglycerol-n" as used herein is meant to refer to the main species of polyglycerol that is found in a given preparation, but does not necessarily exclude the presence of other polyglycerols in lesser relative amounts, as long as the other polyglycerols do not interfere with the preparation of a wax, emulsifier, emulsion, or composition of the present invention.

In some embodiments, glycerol stearate can be produced by esterifying about 0.8 to 1.2 equivalents of stearic acid with 1.0 equivalent of glycerol. In some embodiments, the glycerol stearate can be produced by esterifying about 1.0 equivalents of stearic acid with 1.0 equivalent of glycerol.

Waxes of the present invention can be prepared by melting the polyglyceryl fatty acid ester, slowly adding the glycerol fatty acid ester and then the fatty alcohol while mixing. In some embodiment, the melting can be performed at about 80° C. to about 100° C. In another embodiment, the melting can be performed at about 90° C. The mixture can then be discharged and flaked to form a solid wax.

In some embodiments, the principal components can be mixed in the following ratios (all by weight): 20 to 50 parts, preferably 35 to 40 parts, of the polyglyceryl fatty acid ester (a); 25 to 40 parts of the glycerol fatty acid ester (b); and 25 to 35 parts of fatty alcohol (c). In another embodiment, the wax produced has a melting point between about 54° C. to about 65° C. In another embodiment, the wax produced has a melting point ranging between about 55° C. and about 62° C.

Water Gel Preparation

In some embodiments, a water gel (or hydrophilic gel) can be produced by melting the wax of the present invention (e.g., 5% by weight) in warm water (e.g., about 75° C.) and mixing. This can be done in the presence of preservatives (e.g., phenoxyethanol and parabens), which can be added to the water in the beginning. In another embodiment, the water gel that is produced can remain stable for at least 1 day, 2 days, 1 week, 2 weeks, 3 weeks or 1 month at about 50° C., during which no separation, syneresis, or perceptible change in texture of the gel occurs.

In some embodiments, water gels of the present invention can a viscosity of between about 4,000 and about 9,000 cPs.

Oil-in-Water Emulsion Preparation

In some embodiments, an O/W emulsion can be produced by first preparing an oil phase by melting/mixing the wax of the present invention (e.g., 5% by weight) with a pharmaceutically or cosmetically acceptable oil (e.g., about 10% by weight) and heating (e.g., about 70° C. to about 75° C.), and mixing the oil phase with a water phase, which may also be heated (e.g., about 70° C. to about 75° C.), and may optionally contain preservatives (e.g., phenoxyethanol and parabens) or other additives. The oil phase can be added to the water phase under stirring (e.g., using a homogenizer).

In some embodiments, the oil phase can comprise any suitable oil components which are skin-compatible oil components or component mixtures that are non-water-mixable and which may, for example, be natural oils, fatty acid esters, mono-, di- or triglycerides, or other oils, or mixtures thereof. Preferably, the oils are liquid at ambient temperature, in particular are liquid at 20° C. or at 25° C. They can contain certain amounts of solid lipid components (e.g. fats) as long as the complete oily mixture is liquid at ambient temperature or at the temperatures mentioned above. Other oils which can be incorporated comprise natural oils or fats, or natural oil derivatives, in particular of vegetable origin. Examples are almond oil, soybean oil, sunflower oil, safflower oil, corn oil, canola oil, borage oil, evening primrose oil, grape seed oil, wheat germ oil, avocado oil, jojoba oil, kernel oil, sesame oil, walnut oil, linseed oil, palm oil, olive oil, macadamia oil, castor oil, rapeseed oil, peanut oil, coconut oil, and turnip seed oil.

In some embodiments, the viscosity of the resulting oil-in-water emulsion can be about 9,000 to about 13,000 cPs. In another embodiment, the resulting emulsion is stable (i.e., there is no break in the emulsion) for at least 1 day, 2 days, 1 week, 2 weeks, 3 weeks or 1 month at about 50° C.

Methods and Uses

In some embodiments, compositions (e.g., water gels and O/W emulsions) produced from or comprising waxes of the present invention can provide cosmetic and/or therapeutic benefits, such as reducing and/or preventing skin barrier function disruption, accelerating skin barrier function recovery or repair, reducing trans-epidermal water loss (TEWL), hydrating or moisturizing skin, or any combination thereof. Accordingly, in some aspects, the present invention relates to a method for reducing and/or preventing skin barrier function disruption, accelerating skin barrier function recovery or repair, reducing trans-epidermal water loss (TEWL), hydrating or moisturizing skin, or any combination thereof, the method comprising administering to the skin of a subject a composition (e.g., water gels and oil-in-water emulsions) produced from or comprising waxes of the present invention. In some embodiments, the skin barrier function disruption, TEWL, tissue dehydration or dryness is from UV-induced skin barrier damage. For example, compositions of the present invention can be applied topically to skin (e.g., at about 2 mg/cm$^2$) regularly for a period of time, or once, prior to, or after, UV exposure to protect or repair skin barrier function, or to hydrate or moisture skin, which can be assessed for example by measuring a reduction in TEWL as compared to untreated, UV-exposed controls.

In some aspects, the waxes of the present invention are useful for the manufacture of a product (e.g., pharmaceutical or cosmetic product) for use in reducing and/or preventing skin barrier function disruption, accelerating skin barrier function recovery or repair, reducing trans-epidermal water loss (TEWL), hydrating or moisturizing skin, or any combination thereof.

Formulations and Additives

In some embodiments, compositions of the present invention can be in the form of creams, milks, gel creams, fluid lotions, and vaporizable fluid lotions. When the composition according to the present invention possesses appropriate fluidity characteristics, it can also serve for the impregnation of substrates consisting of synthetic or natural, woven or nonwoven textile fibers, or papers, for constituting articles, for example wipes, intended for care, protection or cleaning of the skin, of the scalp or of the hair, or for example papers for sanitary or household use.

In some embodiments, compositions of the present invention can be used by application on the skin, hair or scalp, whether it is direct application in the case of a cosmetic, dermocosmetic, dermo-pharmaceutical or pharmaceutical composition, or indirect application in the case of a product for the care, protection, or cleaning of the body, being in the form of a textile article, for example a wipe, or of paper, for example a paper for sanitary use, intended to be in contact with the skin, hair or scalp.

The present invention also relates to the cosmetic use of the composition as defined herein for cleaning, for protection and/or for care of the skin, hair or scalp. Compositions of the present invention can be used for care or for protection of the skin, for example as cream, as milk or as lotion for care or for protection of the face, hands and body.

In some embodiments, compositions according to the present invention can also be used as a product for protecting the skin against the sun's rays, and as a skin make-up product. In a particular embodiment, compositions according to the present invention can include an ultraviolet absorber. Examples of the ultraviolet absorbers include benzoic acid ultraviolet absorbers such as p-aminobenzoic acid (hereinafter, abbreviated as "PABA"), PABA monoglycerin ester, N,N-dipropoxy PABA ethyl ester, N,N-diethoxy PABA ethyl ester, N,N-dimethyl PABA ethyl ester, N,N-dimethyl PABA butyl ester, and N,N-dimethyl PABA ethyl ester; anthranilic acid ultraviolet absorbers such as homomethyl-N-acetyl anthranilate; salicylic acid ultraviolet absorbers such as amyl salicylate, menthyl salicylate, homomethyl salicylate, octyl salicylate, phenyl salicylate, benzyl salicylate, and p-isopropanol phenyl salicylate; cinnamic acid ultraviolet absorbers such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, octyl-p-methoxy cinnamate (2-ethylhexyl-p-methoxy cinnamate), 2-ethoxyethyl-p-methoxycinnamate, cyclohexyl-p-methoxycinnamate, ethyl-.alpha.-cyano-.beta.-phenyl cinnamate, 2-ethylhexyl-.alpha.-cyano-.beta.-phenyl cinnamate, and glycerylmono-2-ethylhexanoyl-diparamethoxycinnamate; benzophenone ultraviolet absorbers such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethyl hexyl-4'-phenylbenzophenone-2-carboxylate, 2-hydroxy-4-n-octoxybenzophenone, and 4-hydroxy-3-carboxybenzophenone; 3-(4'-methylbenzylidene)-d,l-camphor; 3-benzylidene-d,l-camphor; urocanic acid; ethyl urocanate ester; 2-phenyl-5-methylbenzoxazole; 2,2'-hydroxy-5-methylphenylbenzotriazole; 2-(2'-hydroxy-5'-t-octylphenyl)benzotriazole; 2-(2'-hydroxy-5'-methylphenyl)benzotriazole; dibenzalazine; dianisoylmethane; 4-methoxy-4'-t-butyldibenzoylmethane; 5-(3,3-dimethyl-2-norbornylidene)-3-pentan-2-one; 2,4,6-trianilino-p-(carbo-2'-ethylhexyl-t-oxy)-1,3,5-triazine; and 4-tert-butyl-4'-methoxydibenzoylmethane. These ultraviolet absorbers may be used alone or in a combination of two or more thereof.

In some embodiments, compositions of the present invention can include a moisturizer. Examples of moisturizers include polyethylene glycol (PEG1500), propylene glycol, 1,3-propanediol, 3-methyl-1,3-butanediol, glycerol, 1,3-butylene glycol, xylitol, sorbitol, maltitol, chondroitin sulfuric acid, hyaluronic acid, mucoitin sulfuric acid, Trichosanthis semen acid, atelocollagen, cholesteryl-12-hydroxy stearate, sodium lactate, urea, bile salt, dl-pyrrolidone carboxylate, short-chain soluble collagen, diglycerin (EO) PO adducts, *Rosa roxburghii* extracts, yarrow extracts and melilot extracts. These moisturizers may be used alone or in a combination of two or more thereof.

In some embodiments, compositions of the present invention can include a thickener. Examples of thickeners include gum arabic, carrageenan, Karaya gum, gum tragacanth, carob gum, quince seed (marmelo), casein, dextrin, gelatin, sodium pectinate, sodium alginate, methylcellulose, ethylcellulose, CMC, hydroxyethyl cellulose, hydroxypropyl cellulose, PVA, PVM, PVP, sodium polyacrylate, carboxyvinyl polymer, locust bean gum, guar gum, tamarind gum, dialkyl dimethyl ammonium cellulose sulfate, xanthan gum, magnesium aluminum silicate, bentonite, hectorite, quaternary ammonium salt-based cation-modified bentonite, quaternary ammonium salt-based cation-modified hectorite, and decaglycerin fatty acid ester eicosadioate condensate. These thickeners may be used alone or in a combination of two or more thereof.

In some embodiments, compositions of the present invention can include a preservative. Without being so limited, preservative are ingredients capable of retarding or preventing microbial or chemical spoilage and protecting against discoloration, such as DMDM hydantoin, methylparaben, propylparaben, phenoxyethanol, ethylparaben, butylparaben, imidazolidinyl urea, diazolidinyl urea, quaternium-8, quaternium-14, quaternium-15, propylene glycol, dehydroacetic acid, methylchloroisothiazolinone, methylisothiazolinone and germaben. These preservatives may be used alone or in a combination of two or more thereof.

In some embodiments, compositions of the present invention can include a pH adjuster. Examples of pH adjusters include edetic acid, disodium edetate, citric acid, sodium citrate, sodium hydroxide, potassium hydroxide, and triethanolamine. These pH adjusters may be used alone or in a combination of two or more thereof.

In some embodiments, compositions of the present invention can include a plant or algae extract. Examples of plant extracts include extracts of: aloe vera, artichoke, bamboo, bearberry, birch tree, borage, butcher's broom, *capsicum*, centella, chamomile, coffee, cucumber, devil's claw, dragonfruit, *eucalyptus*, fenugreek, flax, ginger, *ginseng*, grapefruit, green tea, *Hamamelis*, hawthorn, honeysuckle, hops, horse chestnut tree, horsetail, iris, jasmine, jojoba, kidney bean, kola, lavender, lemon, liquorice, lotus, *magnolia* tree, marshmallow, milk thistle, millet, myrrh tree, neem tree, noni tree, oat, olive tree, orchid, oregano, passion fruit, peppermint, pineapple, pomegranate tree, *quinoa*, raspberry bush, red clover, rice, rose, rose hips, rosemary, sage, saw *palmetto*, schizandra, sea fennel, sesame, strawberry, sunflower, thyme, tomato, turmeric, violet, walnut tree, watercress, wheat, white water lily, white willow, winter cherry, witch hazel, ylang-ylang, and *yucca* extracts. Examples of algae extracts include: bladderwrack, devil's apron, dulse, dunaliella, himanthalia, *laminaria*, pelvetia, *porphyra*, and *spirulina* extracts.

In some embodiments, compositions of the present invention can include an antioxidant. Examples of antioxidants include, but are not limited to, amino acids such as glycine, histidine, tyrosine, trytophan and derivatives thereof, imidazoles such as urocanic acid and derivatives thereof, peptides, such as D,L-carnosine, D-carnosine, L-carnosine and derivatives thereof such as anserine, carotinoids, carotenes such as .alpha.-carotone, .beta.-carotene, lycopene, and derivatives thereof, chlorogenic acid and derivatives thereof, lipoic acid and derivatives thereof such as dihydrlipoic acid, aurothioglycose, propylthiouracil and other thiols such as thioredoxin, glutathione, cysteine, cystine, cystamine and glycosyl, N-acetyl, methyl, ethyl, propyl, amyl, butyl, lauryl, palmitoyl, oleyl, .alpha.-linoleyl, cholesteryl and glyceryl esters and salts thereof, dilauryl thiodipropionate, distearyl thiodipropionate, thiodipropionic acid and derivatives thereof such as esters, ethers, peptides, lipids, nucleotides, nucleosides, and salts, sulfoximine compounds such as buthionine sulfoximines, homocysteine sulfoximine, buthionine sulfones, penta-, hexa-, hepta-thionine sulfoximine, unsaturated fatty acids and derivatives thereof such as .alpha.-linolenic acid, linoleic acid, oleic acid, folic acid and derivatives thereof, ubiquinone and ubiquinol and derivatives thereof, vitamin C and derivatives thereof such as ascorbyl palmitate, magnesium ascorbyl phosphate, ascorbyl acetate, tocopherals and derivatives such as vitamin E acetate, vitamin A and derivatives such as vitamin A palmitate, vitamin B and derivatives thereof, coniferyl benzoate of benzoin resin, rutinic acid and derivatives thereof, .alpha.-glycosylrutin, ferulic acid, furfurylidene glucitol, carnosine, butyl hydroxytoluene, trihydroxy-butyrophenone, uric acid and derivatives thereof, mannose and derivatives thereof, superoxide dismutase, zinc and derivatives thereof such as ZnO, ZnSO$_4$, selenium and derivatives thereof such as selenium methionine, stilbene and derivatives thereof such as stilbene oxide, trans-stilbene oxide and the like. In particular exemplary embodiments, the one or more antioxidants may include vitamin B, nordihydroguaiaretic acid, butylated hydroxyanisole (BHA), butylated hydroxytoluene (BHT), propyl gallate, erythorbate acid, sodium erythorbate, ascorbir palmitate, ascorbir stearate, butyl hydroxyanisole, and gallic esters. These antioxidants may be used alone or in a combination of two or more thereof.

In some embodiments, compositions of the present invention can include chelating agents or sequestering agents (sequestrants). Examples of chelating agents include EDTA, disodium EDTA, trisodium EDTA, EGTA, disodium EGTA, trisodium EGTA, citric acid, phosphoric acid, and succinic acid.

In some embodiments, compositions of the present invention can include opacifying agents. Examples of pacifying agents include higher fatty alcohols such as cetyl, stearyl, cetostearyl alcohol, arachidyl and behenyl alcohols, solid esters such as cetyl palmitate, glyceryl laurate, stearamide MEA-stearate, high molecular weight fatty amides and alkanolamides and various fatty acid derivatives such as propylene glycol and polyethylene glycol esters. In other embodiments, opacifying agents may include inorganic materials such as, for example, magnesium aluminum silicate, zinc oxide, titanium dioxide or other sunblocking agents.

In some embodiments, compositions of the present invention can include one or more further topically active ingredients useful in skincare. Such active ingredients may include one or more of the following: antimicrobial or antibacterial compounds, for example selected from the following: triclosan, neomycin, clindamycin, polymyxin, bacitracin, benzoyl peroxide, hydrogen peroxide, tetracylines such as doxycycline or minocycline, sulfa drugs such as sulfacetamide, penicillins, cephalosporins such as cephaiexin, and quinolones such as lomefloxacin, olfoxacin or trovafloxacin; antiviral compounds, for example selected from acyclovir, tamvir, and penciclovir; antifungal compounds, for example selected from the following: framesol, clotrimazole, ketoconazole, econazole, fluconazole, calcium or zinc undecylenate, undecylenic acid, butenafine hydrochloride, ciclopirox olaimine, miconazole nitrate, nystatin, sulconazole, and terbinafine hydrochloride; anti-inflammatory compounds, for example selected from the following: steroidal agents selected from hydrocortisone, fluocinolone acetonide, halcinonide, halobetasol propionate, clobetasol propionate, betamethasone dipropionate, betamethasone valerate, and triamcinolone acetonide, and non-steroidal anti-inflammatory agents selected from aspirin, ibuprofen, ketoprofen, naproxen, aloe vera gel, aloe vera, licorice extract, pilewort or zinc; anthelmintic compounds, for example metronidazole.

In some embodiments, compositions of the present invention can include a fragrance. Examples of fragrance include plant perfumes such as rose oil, jasmine oil, and lavender oil; and synthetic perfumes such as limonene, citral, linalool, and eugenol. These perfumes may be used alone or in a combination of two or more thereof.

Active and functional ingredients for use in compositions of the present invention, including those listed above, may be plant extracts, algae extracts, fruit extracts, vegetable extracts, leguminous plant extracts, ferments, proteolytic hydrolysates, peptides, yeast extracts and its derivatives, microorganism extracts, animal derivative extracts and/or synthetic compounds.

The present invention is illustrated in further details by the following non-limiting examples.

EXAMPLES

Example 1

Wax Preparation with Polyglyceryl-2 Stearate

An embodiment of a wax of the present invention was prepared having the following components:
- ($A_1$) Polyglyceryl-2 stearate: 1.1 equivalents of pure (>95%) stearic acid, using methods well known in the art, was esterified with 1.0 equivalent of Polyglyceryl-2 (Diglycerol: two glycerol monomeric units >90%).
- (B) Glycerol stearate: 1.0 equivalent of pure (>95%) stearic acid, using methods well known in the art, was esterified with 1.0 equivalent of pure glycerol (>99%).
- (C) Pure stearyl alcohol (>95%).

About 35 g of component ($A_1$) (Polyglyceryl-2 stearate) was melted at about 90° C., and about 35 g of component (B) was then slowly added. At the end, keeping the temperature at about 90° C., 30 g of component (C) was slowly added and the mixture was stirred at about 90° C. for about 30 minutes. At the end, the mixture was discharged and flaked to form a solid wax having a melting point of 62° C.

Example 2

Wax Preparation with Polyglyceryl-3 Stearate

Another embodiment of a wax of the present invention was prepared having the following components:
- ($A_2$) Polyglyceryl-3 stearate: 1.1 equivalents of pure (>95%) stearic acid, using methods well known in the art, was esterified with 1.0 equivalent of Polyglyceryl-3 (Triglycerol: three glycerol monomeric units >50%).
- (B) Glycerol stearate: 1.0 equivalent of pure (>95%) stearic acid, using methods well known in the art, was esterified with 1.0 equivalent of pure glycerol (>99%).
- (C) Pure stearyl alcohol (>95%).

About 35 g of component ($A_2$) (Polyglyceryl-3 stearate) was melted at about 90° C., and about 35 g of component (B) was then slowly added. At the end, keeping the temperature at about 90° C., 30 g of component (C) was slowly added and the mixture was stirred at about 90° C. for about 30 minutes. At the end, the mixture was discharged and flaked to form a solid wax having a melting point ranging from 55° C.-60° C.

Example 3

Wax Preparation with Polyglyceryl-4 Stearate

Another embodiment of a wax of the present invention was prepared having the following components:
- ($A_3$) Polyglyceryl-4 stearate: 1.1 equivalents of pure (>95%) stearic acid, using methods well known in the art, was esterified with 1.0 equivalent of Polyglyceryl-4 (Tetraglycerol: four glycerol monomeric units >40%).
- (B) Glycerol stearate: 1.0 equivalent of pure (>95%) stearic acid, using methods well known in the art, was esterified with 1.0 equivalent of pure glycerol (>99%).
- (C) Pure stearyl alcohol (>95%).

About 35 g of component ($A_3$) (Polyglyceryl-4 stearate) was melted at about 90° C., and about 35 g of component (B) was then slowly added. At the end, keeping the temperature at about 90° C., 30 g of component (C) was slowly added and the mixture was stirred at about 90° C. for about 30 minutes. At the end, the mixture was discharged and flaked to form a solid wax having a melting point ranging from 54° C.-59° C.

Example 4

Preparation of Water Gels from Example 1-3 Waxes

The waxes prepared as described in Example 1 ("Example 1 wax"), Example 2 ("Example 2 wax") and Example 3 ("Example 3 wax") were melted separately in warm water (about 75° C.) in the presence of preservatives (e.g., phenoxyethanol and parabens) and stirred with a homogenizer. A gel-in-water system ("water gel") was then produced according to Table 1 (all quantities in percentages are by weight).

TABLE 1

Water Gel

| | |
|---|---|
| Aqua | 94.6% |
| Example 1, 2 or 3 wax | 5% |
| Phenoxyethanol and Parabens | 0.4% |

All three waxes (Examples 1, 2 and 3) were able to produce water gels.

The viscosity from the water gel produced from the Example 1 wax was 4,300-5,000 cPs (Brookfield, S92; 10 rpm; 12%) and this water gel was stable for more than a month at 50° C., during which no separation, syneresis, or change in texture of the gel was observed.

The viscosity from the water gel produced from the Example 2 wax was 7,200-8,800 cPs (Brookfield, S92; 10 rpm; 21%) and this water gel was stable for more than a month at 50° C., during which no separation, syneresis, or change in texture of the gel was observed.

The viscosity from the water gel produced from the Example 3 wax was 4,000-4,500 cPs (Brookfield, S92; 10 rpm; 11%) and this water gel was stable for more than a month at 50° C., during which no separation, syneresis, or change in texture of the gel was observed.

Example 5

Production of Oil-in-Water Emulsions from Example 1-3 Waxes

Three separate O/W emulsions were prepared from the waxes of Examples 1, 2 and 3 according to Table 2 (all quantities in percentages are by weight).

TABLE 2

| Water Phase (Phase A): | |
|---|---|
| Aqua | 84.6% |
| Phenoxyethanol and Parabens | 0.4% |
| Oil Phase (Phase B): | |
| Examele 1, 2 or 3 wax | 5% |
| Sweet almond oil | 10% |

Phase B was heated to 70-75° C. and was added to Phase A (also heated up to 70-75° C.) under stirring using a homogenizer.

All three waxes (Examples 1, 2 and 3) were able to produce a stable cream (O/W emulsion).

The cream produced from the Example 1 wax had a viscosity of 9,800-11,000 cPs (Brookfield, S92; 10 rpm; 26%); and this O/W formulation was stable for more than a month at 50° C., during which no separation, syneresis, or change in texture of the cream was observed.

The cream produced from the Example 2 wax had a viscosity of 10,700-12,700 cPs (Brookfield, S92; 10 rpm; 31%); and this O/W formulation was stable for more than a month at 50° C., during which no separation, syneresis, or change in texture of the cream was observed.

The cream produced from the Example 3 wax had a viscosity of 5,500-6,700 cPs (Brookfield, S92; 10 rpm; 16%); and this O/W formulation was stable for more than a month at 50° C., during which no separation, syneresis, or change in texture of the cream was observed.

Example 6

Synergistic Interaction Between Example 1-3 Wax Components for Water Gel Formation To explore synergistic interaction between each of the principal components [(A), (B) and (C)] of the waxes of Examples 1, 2 and 3, the components were tested individually or in different combinations for their ability to prepare stable gel-in-water systems (water gel). Accordingly, different combinations of components as indicated Table 3 (Samples 1-15) were prepared and formulated into corresponding water gels according to Table 4 (all quantities in percentages are by weight).

TABLE 3

| Sample | Component(s) |
|---|---|
| 1 | $A_1$ (Polyglyceryl-2 stearate) only |
| 2 | $A_2$ (Polyglyceryl-3 stearate) only |
| 3 | $A_3$ (Polyglyceryl-4 stearate) only |
| 4 | B (Glyceryl stearate) only |
| 5 | C (Stearyl alcohol) only |
| 6 | $A_1$ + B |
| 7 | $A_2$ + B |
| 8 | $A_3$ + B |
| 9 | $A_1$ + C |
| 10 | $A_2$ + C |
| 11 | $A_3$ + C |
| 12 | B + C |
| 13 | Example 1 wax ($A_1$ + B + C) |
| 14 | Example 2 wax ($A_2$ + B + C) |
| 15 | Example 3 wax ($A_3$ + B + C) |

TABLE 4

| Water gel formulations 1-15 | |
|---|---|
| Aqua | 94.6% |
| Phenoxyethanol and Parabens | 0.4% |
| Tested Gelling agent (one of Samples 1-15) | 5% |

Each of Samples 1-15 were separately added to warm water (about 70° C.) in the presence of preservatives (phenoxyethanol and parabens) and mixed with a homogenizer. All resulting water gels were subjected to stability testing. Stability of each of the prepared water gels at about 50° C. was assessed after 1 week, 2 weeks, 3 weeks, and 1 month. The results are summarized in Table 5.

TABLE 5

| Water gel formulation | Components | Gel Formation | 1 week | 2 weeks | 3 weeks | 1 month |
|---|---|---|---|---|---|---|
| 1 | $A_1$ | No | ND | ND | ND | ND |
| 2 | $A_2$ | No | ND | ND | ND | ND |
| 3 | $A_3$ | No | ND | ND | ND | ND |
| 4 | B | No | ND | ND | ND | ND |
| 5 | C | No | ND | ND | ND | ND |
| 6 | $A_1$ + B | No | ND | ND | ND | ND |
| 7 | $A_2$ + B | No | ND | ND | ND | ND |
| 8 | $A_3$ + B | No | ND | ND | ND | ND |
| 9 | $A_1$ + C | No | ND | ND | ND | ND |
| 10 | $A_2$ + C | No | ND | ND | ND | ND |
| 11 | $A_3$ + C | No | ND | ND | ND | ND |
| 12 | B + C | No | ND | ND | ND | ND |
| 13 | Example 1 wax ($A_1$ + B + C) | Yes | Ok | Ok | Ok | Ok |
| 14 | Example 2 wax ($A_2$ + B + C) | Yes | Ok | Ok | Ok | Ok |
| 15 | Example 3 wax ($A_3$ + B + C) | Yes | Ok | Ok | Ok | Ok |

ND = No stability control due to no gel formation

Of the formulations that were tested in this Example, only the Examples 1, 2 and 3 waxes comprising components A, B and C (Formulations 13, 14 and 15) were able to produce water gels. Formulations including only one component (Formulations 1-5) and formulations lacking one of the three components (Formulations 6-12) were not able to produce water gels. These results suggest that components A, B and C act synergistically to enable stable water gel formation.

Example 7

Synergistic Interaction Between Example 1-3 Wax Components for O/W Emulsion Formation To explore synergistic interaction between each of the principal components [(A), (B) and (C)] of the waxes of Examples 1, 2 and 3, the components were tested individually or in different combinations for their ability to prepare stable O/W emulsions. Accordingly, different combinations of components as indicated in Table 6 (Samples 1-15) were prepared and formulated into corresponding O/W emulsions according to Table 7 (all quantities in percentages are by weight).

TABLE 6

| Sample | Component(s) |
|---|---|
| 1 | $A_1$ (Polyglyceryl-2 stearate) only |
| 2 | $A_2$ (Polyglyceryl-3 stearate) only |
| 3 | $A_3$ (Polyglyceryl-4 stearate) only |
| 4 | B (Glyceryl stearate) only |
| 5 | C (Stearyl alcohol) only |
| 6 | $A_1$ + B |
| 7 | $A_2$ + B |
| 8 | $A_3$ + B |
| 9 | $A_1$ + C |
| 10 | $A_2$ + C |
| 11 | $A_3$ + C |
| 12 | B + C |
| 13 | Example 1 wax ($A_1$ + B + C) |
| 14 | Example 2 wax ($A_2$ + B + C) |
| 15 | Example 3 wax ($A_3$ + B + C) |

TABLE 7

| Water Phase (Phase A): | |
|---|---|
| Aqua | 84.6% |
| Phenoxyethanol and Parabens | 0.4% |
| Oil Phase (Phase B): | |
| Tested Oil-in-water (one of Samples 1-15) | 5% |
| Sweet almond Oil | 25% |

Phase B was heated to 70-75° C. and was added to Phase A (also heated up to 70-75° C.) under stirring using a homogenizer. Stability of each of the prepared emulsions at about 50° C. was assessed at time=0, after 24 h, 48 h, 1 week, 2 weeks, 3 weeks and 1 month. The results are summarized in Table 8, and the symbol ("/") indicates an emulsion break, after which stability testing was stopped.

TABLE 8

| Oil-in-water formulation | Tested Components | Emulsion time = 0 | 24 h | 48 h | 1 week | 2 weeks | 3 weeks | 1 month |
|---|---|---|---|---|---|---|---|---|
| 1 | $A_1$ | Yes | / | ND | ND | ND | ND | ND |
| 2 | $A_2$ | Yes | Ok | / | ND | ND | ND | ND |
| 3 | $A_3$ | Yes | Ok | Ok | / | ND | ND | ND |
| 4 | B | No | ND | ND | ND | ND | ND | ND |
| 5 | C | No | ND | ND | ND | ND | ND | ND |
| 6 | $A_1$ + B | Yes | Ok | / | ND | ND | ND | ND |
| 7 | $A_2$ + B | Yes | Ok | / | ND | ND | ND | ND |
| 8 | $A_3$ + B | Yes | Ok | Ok | / | ND | ND | ND |
| 9 | $A_1$ + C | Yes | Ok | / | ND | ND | ND | ND |
| 10 | $A_2$ + C | Yes | Ok | / | ND | ND | ND | ND |
| 11 | $A_3$ + C | Yes | Ok | Ok | / | ND | ND | ND |
| 12 | B + C | Yes | / | ND | ND | ND | ND | ND |
| 13 | Example 1 wax ($A_1$ + B + C) | Yes | Ok | Ok | Ok | Ok | Ok | Ok |
| 14 | Example 2 wax ($A_2$ + B + C) | Yes | Ok | Ok | Ok | Ok | Ok | Ok |
| 15 | Example 3 wax ($A_3$ + B + C) | Yes | Ok | Ok | Ok | Ok | Ok | Ok |

/ = Emulsion breaks
ND = No stability control due to emulsion break

Of the formulations that were tested in this Example, only the Examples 1, 2 and 3 waxes comprising components A, B and C (Formulations 13, 14 and 15) were able to produce O/W emulsions that remained stable for 1 week or more. Formulations including only one component (Formulations 1-5) and formulations lacking one of the three components (Formulations 6-12) were either not able to form an emulsion at all (Formulations 4 and 5), or were not able to produce an emulsion that remained stable for 1 week or more (Formulations 1-3 and 6-12). These results suggest that components A, B and C of the waxes of the present invention can act synergistically to enable the formation of stable oil-in-water emulsions.

Example 8

Prevention of UV-Induced Skin Barrier Damage by Water Gel Prepared from Example 1 Wax A water gel prepared from the Example 1 wax, prepared as described in Example 4, was evaluated for the prevention of UV-induced skin barrier damage.

The UV exposure intensity was calibrated to induce 1.5 MED (1 MED or Minimal Erythema Dose, which corresponds to the minimum amount of UVB radiation required to produce redness 24 hours after skin exposure). The test was carried out on a panel of 10 healthy human volunteers. Selected skin areas were kept untreated and unexposed to UV as controls. Other skin areas were treated for a period of 10 days (from Day 1 to Day 10) preceding UV exposure. Topical treatments (2 mg/cm$^2$) consisted of a placebo gel (Table 9, all quantities in percentages are by weight) or the water gel prepared from the Example 1 wax (Table 1).

TABLE 9

| Placebo gel | |
|---|---|
| Aqua | 94.6% |
| Cetearyl alcohol | 3% |
| Ceteareth-20 | 2% |
| Phenoxyethanol and Parabens | 0.4% |

Specific skin sites were exposed to UV light on Day 11. On Day 12, 20±4 hours after UV exposure, skin barrier function was assessed to measure the protective effect of the treatments. Trans-epidermal water loss (TEWL) was assessed using the apparatus Tewameter 300® (Courage+ Khazaka, electronic GmbH) and skin erythema was measured using the apparatus Mexameter® MX 18 (Courage+ Khazaka, electronic GmbH).

The water gel prepared from the Example 1 wax ("Example 1 water gel"), when applied as a preventive treatment, resulted in a reduction of the UV-induced increase in TEWL (see Table 10).

TABLE 10

| | UV-induced increase in TEWL[2] |
|---|---|
| Control (untreated skin) | 83.5% |
| Placebo gel | 78.9% |
| Example 1 water gel | 57.7% (p < 0.029)[1] |

[1]Statistically significant when compared to Placebo gel
[2]Compared to non-irradiated skin (baseline)

This demonstrates that formulations comprising the Example 1 wax can provide protection from UV-induced skin barrier function loss.

Example 9

Repairing/Recovery Effect on UV-Induced Skin Barrier Damage by Water Gel Prepared from Example 1 Wax A water gel prepared from the Example 1 wax, formulated as described in Example 4, was evaluated for its repairing/recovery effect on UV-induced skin barrier damage.

Some skin areas on the 10 healthy human volunteers tested in Example 8 were topically treated only one day after the UV-induced skin barrier damage (i.e., on Day 12). The treatment schedule is shown schematically in FIG. 1. In this Example, skin was post-treated with one topical application (2 mg/cm$^2$) of a placebo gel (Table 9) or Example 1 water gel (Table 1). The repairing/recovery effect of the treatments for skin barrier function was assessed by measuring TEWL levels (as described in Example 8) at different times following the topical application of the formulations (i.e., at 30 minutes, 1 hour, 2 hours and 24 hours). The TEWL levels measured at different times were then compared to baseline levels (i.e., TEWL levels of untreated skin one day following UV exposure; at t=0 minutes) and the variation in TEWL values are shown in Table 11.

Results obtained in this experiment revealed that applying the Example 1 water gel after UV-induced skin barrier damage significantly reduces the extent of trans-epidermal water loss and helps improve recovery from skin barrier damage (Table 11).

TABLE 11

| | Variation of TEWL values | | | |
|---|---|---|---|---|
| | After 30 min | After 1 hour | After 2 hours | After 24 hours |
| Control (untreated skin) | −0.9% | 2.0% | −1.3% | −7.2% |
| Placebo gel | −10.5% | −10.8% | −12.3% | −13.1% |
| Example 1 water gel | −12.9% (p = 0.030)[1] | −16.9% (p = 0.035)[1] | −17.8% (p = 0.024)[1] | −22.9% (p < 0.006)[1] |

[1]Statistically significant when compared to Placebo gel

This supports the therapeutic action of the Example 1 wax formulation in promoting skin barrier function.

Although the present invention has been described hereinabove by way of specific embodiments thereof, it can be modified, without departing from the spirit and nature of the subject invention as defined in the appended claims.

The invention claimed is:

1. A wax having oil-in-water (O/W) emulsion-forming properties, said wax comprising:
 (a) about 20 to about 50 parts of a polyglyceryl fatty acid ester, having a fatty acid carbon chain length of $n_1$;
 (b) about 25 to about 40 parts of a glycerol fatty acid ester, having a fatty acid carbon chain length of $n_2$; and
 (c) about 25 to about 35 parts of a fatty alcohol, having a fatty carbon chain length of $n_3$;
wherein each of $n_1$, $n_2$, and $n_3$ represents any integer in the range of 12 to 22, and wherein said wax forms an O/W emulsion in the absence of a co-emulsifier, a polar or an ionic surfactant, an ethoxylated product, a propoxylated product, a rheological modifier, a gelling agent, or any combination thereof wherein said wax can form (i) a stable O/W emulsion for at least 1 week at about 50° C.; and (ii) a gel-in-water that is stable for at least 1 week at about 50° C.

2. The wax of claim 1, wherein (a) is a polyglyceryl-2 fatty acid ester, a polyglyceryl-3 fatty acid ester, or a polyglyceryl-4 fatty acid ester.

3. The wax of claim 1, wherein:
 (i) the fatty acid of (a) is saturated;
 (ii) the fatty acid of (b) is saturated;
 (iii) the fatty alcohol of (c) is saturated; or
 (iv) any combination of (i) to (iii).

4. The wax of claim 1, wherein each of $n_1$, $n_2$, and $n_3$ represent any integer (i) in the range of 14 to 20; or (ii) in the range of 16 to 18.

5. The wax of claim 1, wherein the difference between the integers represented by $n_1$ and $n_2$, $n_1$ and $n_3$, and $n_2$ and $n_3$ is (i) less than or equal to 4; (ii) less than or equal to 3; (iii) less than or equal to 2; or (iv) less than or equal to 1.

6. The wax of claim 1, wherein $n_1=n_2=n_3$.

7. The wax of claim 1, wherein (i) $n_1=18$; (ii) $n_2=18$; and/or (iii) $n_3=18$.

8. The wax of claim 1, wherein said wax comprises (a) about 35 to about 45 parts of said polyglyceryl fatty acid ester.

9. The wax of claim 1, wherein (a) is polyglyceryl stearate; (b) is glyceryl stearate; and/or (c) is stearyl alcohol.

10. The wax of claim 9, wherein said polyglyceryl stearate is: polyglyceryl-2 stearate; polyglyceryl-3 stearate; polyglyceryl-4 stearate; or any combination thereof.

11. The wax of claim 10, wherein said polyglyceryl stearate is integrated according to the following stoichiometry: (i) about 1.0 to about 2.0 equivalents of stearic acid esterified with 1.0 equivalent of polyglyceryl-2, polyglyceryl-3, polyglyceryl-4, or any combination thereof; or (ii) about 1.1 to about 1.2 equivalents of stearic acid esterified with 1.0 equivalent of polyglyceryl-2, polyglyceryl-3, polyglyceryl-4, or any combination thereof.

12. The wax of claim 9, wherein said glyceryl stearate is integrated according to the following stoichiometry: (i) about 0.8 to 1.2 equivalents of at least 95% pure stearic acid, esterified with 1.0 equivalent of at least 95% pure glycerol; or (ii) about 1.0 equivalent of at least 95% pure stearic acid, esterified with 1.0 equivalent of sufficiently pure glycerol.

13. The wax of claim 1, wherein said wax has self-emulsifying properties.

14. The wax of claim 1, wherein said wax does not comprise a co-emulsifier, a polar or an ionic surfactant, an ethoxylated product, a propoxylated product, a rheological modifier, a gelling agent, or any combination thereof.

15. The wax of claim 1, wherein said wax is present in a cosmetic composition.

16. The wax of claim 1, wherein said wax is present in a topical composition.

\* \* \* \* \*